US008043812B2

United States Patent
Seki et al.

(10) Patent No.: US 8,043,812 B2
(45) Date of Patent: Oct. 25, 2011

(54) **METHOD OF DETECTING *STREPTOCOCCUS PNEUMONIAE*, PRIMER SET FOR THE DETECTION AND KIT FOR THE DETECTION**

(75) Inventors: Mitsuko Seki, Tokyo (JP); Hiromasa Tsuda, Tokyo (JP)

(73) Assignee: Nihon University, Tokyo (JP)

( * ) Notice: Subject to any disclaimer, the term of this patent is extended or adjusted under 35 U.S.C. 154(b) by 1008 days.

(21) Appl. No.: 11/665,565

(22) PCT Filed: Aug. 26, 2005

(86) PCT No.: PCT/JP2005/016069
§ 371 (c)(1),
(2), (4) Date: Apr. 17, 2007

(87) PCT Pub. No.: WO2006/043368
PCT Pub. Date: Apr. 27, 2006

(65) Prior Publication Data
US 2009/0087837 A1    Apr. 2, 2009

(30) Foreign Application Priority Data

Oct. 19, 2004  (JP) ................................ 2004-304878
Oct. 29, 2004  (JP) ................................ 2004-317283

(51) Int. Cl.
*C12Q 1/68* (2006.01)

(52) U.S. Cl. .................................... 435/6.12; 435/24.33
(58) Field of Classification Search ............. 435/6, 91.2; 536/22.1, 24.33
See application file for complete search history.

(56) References Cited

U.S. PATENT DOCUMENTS
2003/0207292 A1* 11/2003 Notomi et al. ................... 435/6

OTHER PUBLICATIONS

Seki, M. et al. Loop-mediated amplification method targeting the lytA gene for setection of *Streptococcus pneumoniae*. J Clin Microbiol., vol. 43, No. 4, pp. 1581-1586, Apr. 2005.*
Lowe et al., A computer program for selection of oligonucleotide primers for polymerase chain reactions. Nucleic Acids Research, vol. 18, No. 7, pp. 1757-1761, 1990.*
Whatmore, A.M. et al. The autolysin-encoding gene (lytA) of *Streptococcus pneumoniae* displays restricted alleleic variation despite localized recombination events with genes of pneumococcal bacteriophage encoding cell wall lytic enzymes. Infection and Immunity, vol. 67, No. 9, pp. 4551-4556, 1999.*
Seki, M. et al., J. Clin. Microbial., (Apr. 2005), vol. 43, No. 4, pp. 1581 to 1586.
Sheppard, C.L. et al., J. Medical Microbiology, (Mar. 2004), vol. 53, pp. 189 to 195.
*S. pneumoniae* autolysin (lytA) gene, complete cds, GenBank [Online], Apr. 26, 1993, Accession No. M13812 Retrieved on Nov. 22, 2005, Retrieved from the United States NCBI web site.
Nagamine, K. et al., Mol. Cell. Probes, (2002), vol. 16, pp. 223 to 229.
Gillespie, S.H. et al., J. Clin. Microbial., (1994), vol. 32, No. 5, pp. 1308 to 1311.
Rudolph, K.M. et al., J. Clin. Microbial., (1993), vol. 31, No. 10, pp. 2661 to 2666.

* cited by examiner

*Primary Examiner* — Prabha Chunduru
(74) *Attorney, Agent, or Firm* — Birch, Stewart, Kolasch & Birch, LLP

(57) ABSTRACT

A method of detecting *Streptococcus pneumoniae*, which is characterized in that it comprises amplifying a lytA gene derived from *S. pneumoniae* using a LAMP primer set comprising at least one primer having a nucleotide sequence that is identical to or complementary to a partial sequence in the region ranging from bp 40 to 450 of the nucleotide sequence region of the above-described lytA gene, and then detecting the obtained amplified product.

2 Claims, 10 Drawing Sheets

Fig. 1

```
No.                  10         20         30         40         50         60
Primer                                                                       |---
Base         ATGGAAATTA ATGTGAGTAA ATTAAGAACA GATTTGCCTC AAGTCGGCGT GCAACCATAT No.                  70         80         90        100        110        120
Primer       ---F3--------> |-------F2---------->                <--------------
Base         AGGCAAGTAC ACGCACACTC AACTGGGAAT CCGCATTCAA CCGTACAGAA TGAAGCGGAT
Common part         *                *     *    ***           *                *

No.                 130        140        150        160        170        180
Primer       ---F1------|                        |---------B1----------->
Base         TATCACTGGC GGAAAGACCC AGAATTAGGT TTTTTCTCGC ACATTGTTGG GAACGGTTGC
Common part       ***   *           *          *   *  *   *   *         *   * *

No.                 190        200        210        220        230        240
Primer                  <-----B2-----------|          <------B3--------|
Base         ATCATGCAGG TAGGACCTGT TGATAATGGT GCCTGGGACG TTGGGGGCGG TTGGAATGCT No.                 250        260        270        280        290        300
Base         GAGACCTATG CAGCGGTTGA ACTGATTGAA AGCCATTCAA CCAAAGAAGA GTTCATGACG
Common part          *                                           *             **

No.                 310        320        330        340        350        360
Base         GACTACCGCC TTTATATCGA ACTCTTACGC AATCTAGCAG ATGAAGCAGG TTTGCCGAAA No.                 370        380        390        400        410        420
Base         ACGCTTGATA CAGGGAGTTT AGCTGGAATT AAAACGCACG AGTATTGCAC GAATAACCAA
Common part                  ****     *   *                    *

No.                 430        440        450        460        470        480
Base         CCAAACAACC ACTCAGACCA CGTTGACCCT TATCCATATC TTGCTAAATG GGGCATTAGC
Common part       *

No.                 490        500        510        520        530        540
Base         CGTGAGCAGT TTAAGCATGA TATTGAGAAC GGCTTGACGA TTGAAACAGG CTGGCAGAAG
Common part                      *

No.                 550        560        570        580        590        600
Base         AATGACACTG GCTACTGGTA CGTACATTCA GACGGCTCTT ATCCAAAAGA CAAGTTTGAG
Common part       *                      *          *

No.                 610        620        630        640        650        660
Base         AAAATCAATG GCACTTGGTA CTACTTTGAC AGTTCAGGCT ATATGCTTGC AGACCGCTGG
Common part                                        *

No.                 670        680        690        700        710        720
Base         AGGAAGCACA CAGACGGCAA CTGGTACTGG TTCGACAACT CAGGCGAAAT GGCTACAGGC
Common part       *

No.                 730        740        750        760        770        780
Base         TGGAAGAAAA TCGCTGATAA GTGGTACTAT TTCAACGAAG AAGGTGCCAT GAAGACAGGC
Common part                      *                     *  *

No.                 790        800        810        820        830        840
Base         TGGGTCAAGT ACAAGGACAC TTGGTACTAC TTAGACGCTA AAGAAGGCGC CATGGTATCA
Common part                                           *     *

No.                 850        860        870        880        890        900
Base         AATGCCTTTA TCCAGTCAGC GGACGGAACA GGCTGGTACT ACCTCAAACC AGACGGAACA
Common part                                  *     *

No.                 910        920        930        940        950        960
Base         CTGGCAGACA GGCCAGAATT CACAGTAGAG CCAGATGGCT TGATTACAGT AAAAATAA
Common part       *
```

Log (template DNA initial concentration (copy number))

SEQUENCE LISTING

<160> NUMBER OF SEQ ID NOS: 30

<210> SEQ ID NO 1
<211> LENGTH: 43
<212> TYPE: DNA
<213> ORGANISM: Artificial sequence
<220> FEATURE:
<223> OTHER INFORMATION: synthetic DNA

<400> SEQUENCE: 1
cgccagtgat aatccgcttc attccactca actgggaatc cgc       43

<210> SEQ ID NO 2
<211> LENGTH: 45
<212> TYPE: DNA
<213> ORGANISM: Artificial sequence
<220> FEATURE:
<223> OTHER INFORMATION: synthetic DNA

<400> SEQUENCE: 2
tttctcgcac attgttggga acggccaggc accattatca acagg     45

<210> SEQ ID NO 3
<211> LENGTH: 20
<212> TYPE: DNA
<213> ORGANISM: Artificial sequence
<220> FEATURE:
<223> OTHER INFORMATION: synthetic DNA

<400> SEQUENCE: 3
ccatataggc aagtacacgc                                  20

<210> SEQ ID NO 4
<211> LENGTH: 15
<212> TYPE: DNA
<213> ORGANISM: Artificial sequence
<220> FEATURE:
<223> OTHER INFORMATION: synthetic DNA

<400> SEQUENCE: 4
agcattccaa ccgcc                                       15

<210> SEQ ID NO 5
<211> LENGTH: 44
<212> TYPE: DNA
<213> ORGANISM: Artificial sequence
<220> FEATURE:
<223> OTHER INFORMATION: synthetic DNA

<400> SEQUENCE: 5
gccagtgata atccgcttca ttctgcactc aactgggaat ccgc       44

<210> SEQ ID NO 6
<211> LENGTH: 43
<212> TYPE: DNA
<213> ORGANISM: Artificial sequence
<220> FEATURE:
<223> OTHER INFORMATION: synthetic DNA

<400> SEQUENCE: 6
cgccagtgat aatccgcttc attctactca actgggaatc cgc       43

<210> SEQ ID NO 7
<211> LENGTH: 46
<212> TYPE: DNA

```
<213> ORGANISM: Artificial sequence
<220> FEATURE:
<223> OTHER INFORMATION: synthetic DNA

<400> SEQUENCE: 7
tttctcgcac attgttggga acggcaggca ccattatcaa caggtc        46

<210> SEQ ID NO 8
<211> LENGTH: 16
<212> TYPE: DNA
<213> ORGANISM: Artificial sequence
<220> FEATURE:
<223> OTHER INFORMATION: synthetic DNA

<400> SEQUENCE: 8
aggcaagtac acgcac                                          16

<210> SEQ ID NO 9
<211> LENGTH: 42
<212> TYPE: DNA
<213> ORGANISM: Artificial sequence
<220> FEATURE:
<223> OTHER INFORMATION: synthetic DNA

<400> SEQUENCE: 9
cggtagtccg tcatgaactc ttcttctgag acctatgcag cg              42

<210> SEQ ID NO 10
<211> LENGTH: 43
<212> TYPE: DNA
<213> ORGANISM: Artificial sequence
<220> FEATURE:
<223> OTHER INFORMATION: synthetic DNA

<400> SEQUENCE: 10
atctagcaga tgaagcaggt ttgccttcgt gcaatactcg tgc              43

<210> SEQ ID NO 11
<211> LENGTH: 17
<212> TYPE: DNA
<213> ORGANISM: Artificial sequence
<220> FEATURE:
<223> OTHER INFORMATION: synthetic DNA

<400> SEQUENCE: 11
ttgggggcgg ttggaat                                          17

<210> SEQ ID NO 12
<211> LENGTH: 18
<212> TYPE: DNA
<213> ORGANISM: Artificial sequence
<220> FEATURE:
<223> OTHER INFORMATION: synthetic DNA

<400> SEQUENCE: 12
gagtggttgt ttggttgg                                         18

<210> SEQ ID NO 13
<211> LENGTH: 40
<212> TYPE: DNA
<213> ORGANISM: Artificial sequence
<220> FEATURE:
<223> OTHER INFORMATION: synthetic DNA

<400> SEQUENCE: 13
ctgggtcttt ccgccagtga tcactcaact gggaatccgc                 40
```

```
<210> SEQ ID NO 14
<211> LENGTH: 42
<212> TYPE: DNA
<213> ORGANISM: Artificial sequence
<220> FEATURE:
<223> OTHER INFORMATION: synthetic DNA

<400> SEQUENCE: 14
tctcgcacat tgttgggaac ggtcccaggc accattatca ac                    42

<210> SEQ ID NO 15
<211> LENGTH: 20
<212> TYPE: DNA
<213> ORGANISM: Artificial sequence
<220> FEATURE:
<223> OTHER INFORMATION: synthetic DNA

<400> SEQUENCE: 15
gcgtgcaacc ataggcaa                                               20

<210> SEQ ID NO 16
<211> LENGTH: 20
<212> TYPE: DNA
<213> ORGANISM: Artificial sequence
<220> FEATURE:
<223> OTHER INFORMATION: synthetic DNA

<400> SEQUENCE: 16
gctgcatagg tctcagcatt                                             20

<210> SEQ ID NO 17
<211> LENGTH: 42
<212> TYPE: DNA
<213> ORGANISM: Artificial sequence
<220> FEATURE:
<223> OTHER INFORMATION: synthetic DNA

<400> SEQUENCE: 17
gtctttccgc cagtgataat ccgcactcaa ctgggaatcc gc                    42

<210> SEQ ID NO 18
<211> LENGTH: 43
<212> TYPE: DNA
<213> ORGANISM: Artificial sequence
<220> FEATURE:
<223> OTHER INFORMATION: synthetic DNA

<400> SEQUENCE: 18
ttctcgcaca ttgttgggaa cggtcccagg caccattatc aac                   43

<210> SEQ ID NO 19
<211> LENGTH: 21
<212> TYPE: DNA
<213> ORGANISM: Artificial sequence
<220> FEATURE:
<223> OTHER INFORMATION: synthetic DNA

<400> SEQUENCE: 19
gctgcatagg tctcagcatt c                                           21

<210> SEQ ID NO 20
<211> LENGTH: 41
<212> TYPE: DNA
<213> ORGANISM: Artificial sequence
<220> FEATURE:
<223> OTHER INFORMATION: synthetic DNA
```

<400> SEQUENCE: 20
tgggtctttc cgccagtgat aactcaactg ggaatccgca t           41

<210> SEQ ID NO 21
<211> LENGTH: 40
<212> TYPE: DNA
<213> ORGANISM: Artificial sequence
<220> FEATURE:
<223> OTHER INFORMATION: synthetic DNA

<400> SEQUENCE: 21
ctgggtcttt ccgccagtga tctcaactgg gaatccgcat             40

<210> SEQ ID NO 22
<211> LENGTH: 40
<212> TYPE: DNA
<213> ORGANISM: Artificial sequence
<220> FEATURE:
<223> OTHER INFORMATION: synthetic DNA

<400> SEQUENCE: 22
tgggtctttc cgccagtgat aaactcaact gggaatccgc             40

<210> SEQ ID NO 23
<211> LENGTH: 41
<212> TYPE: DNA
<213> ORGANISM: Artificial sequence
<220> FEATURE:
<223> OTHER INFORMATION: synthetic DNA

<400> SEQUENCE: 23
ccgccagtga taatccgctt cacactcaac tgggaatccg c           41

<210> SEQ ID NO 24
<211> LENGTH: 43
<212> TYPE: DNA
<213> ORGANISM: Artificial sequence
<220> FEATURE:
<223> OTHER INFORMATION: synthetic DNA

<400> SEQUENCE: 24
tctcgcacat tgttgggaac ggccaggcac cattatcaac agg         43

<210> SEQ ID NO 25
<211> LENGTH: 18
<212> TYPE: DNA
<213> ORGANISM: Artificial sequence
<220> FEATURE:
<223> OTHER INFORMATION: synthetic DNA

<400> SEQUENCE: 25

| | |
|---|---|
| tgcatcatgc aggtagga | 18 |

<210> SEQ ID NO 26
<211> LENGTH: 957
<212> TYPE: DNA
<213> ORGANISM: Streptococcus pneumoniae

<400> SEQUENCE: 26

| | |
|---|---|
| atggaaatta atgtgagtaa attaagaaca gatttgcctc aagtcggcgt gcaaccatat | 60 |
| aggcaagtac acgcacactc aactgggaat ccgcattcaa ccgtacagaa tgaagcggat | 120 |
| tatcactggc ggaaagaccc agaattaggt tttttctcgc acattgttgg gaacggttgc | 180 |
| atcatgcagg taggacctgt tgataatggt gcctgggacg ttggggggcgg ttggaatgct | 240 |
| gagacctatg cagcggttga actgattgaa agccattcaa ccaaagaaga gttcatgacg | 300 |
| gactaccgcc tttatatcga actcttacgc aatctagcag atgaagcagg tttgccgaaa | 360 |
| acgcttgata cagggagttt agctggaatt aaaacgcacg agtattgcac gaataaccaa | 420 |
| ccaaacaacc actcagacca cgttgaccct tatccatatc ttgctaaatg gggcattagc | 480 |
| cgtgagcagt ttaagcatga tattgagaac ggcttgacga ttgaaacagg ctggcagaag | 540 |
| aatgacactg gctactggta cgtacattca gacggctctt atccaaaaga caagtttgag | 600 |
| aaaatcaatg gcacttggta ctactttgac agttcaggct atatgcttgc agaccgctgg | 660 |
| aggaagcaca cagacggcaa ctggtactgg ttcgacaact caggcgaaat ggctacaggc | 720 |
| tggaagaaaa tcgctgataa gtggtactat ttcaacgaag aaggtgccat gaagacaggc | 780 |
| tgggtcaagt acaaggacac ttggtactac ttagacgcta agaaggcgc catggtatca | 840 |
| aatgccttta tccagtcagc ggacggaaca ggctggtact acctcaaacc agacggaaca | 900 |
| ctggcagaca ggccagaatt cacagtagag ccagatggct tgattacagt aaaataa | 957 |

<210> SEQ ID NO 27
<211> LENGTH: 21
<212> TYPE: DNA
<213> ORGANISM: Artificial sequence
<220> FEATURE:
<223> OTHER INFORMATION: synthetic DNA

<400> SEQUENCE: 27

| | |
|---|---|
| caaccgtaca gaatgaagcg g | 21 |

<210> SEQ ID NO 28
<211> LENGTH: 22
<212> TYPE: DNA
<213> ORGANISM: Artificial sequence
<220> FEATURE:
<223> OTHER INFORMATION: synthetic DNA

<400> SEQUENCE: 28

| | |
|---|---|
| ttattcgtgc aatactcgtg cg | 22 |

<210> SEQ ID NO 29
<211> LENGTH: 23
<212> TYPE: DNA
<213> ORGANISM: Artificial sequence
<220> FEATURE:
<223> OTHER INFORMATION: synthetic DNA

<400> SEQUENCE: 29

| | |
|---|---|
| atttctgtaa cagctaccaa cga | 23 |

<210> SEQ ID NO 30

```
<211> LENGTH: 23
<212> TYPE: DNA
<213> ORGANISM: Artificial sequence
<220> FEATURE:
<223> OTHER INFORMATION: synthetic DNA

<400> SEQUENCE: 30
gaattccctg tcttttcaaa gtc                                         23
```

METHOD OF DETECTING *STREPTOCOCCUS PNEUMONIAE*, PRIMER SET FOR THE DETECTION AND KIT FOR THE DETECTION

FIELD OF THE INVENTION

The present invention relates to a method of detecting *Streptococcus pneumoniae*, a primer set for detecting *Streptococcus pneumoniae*, and a kit for detecting *Streptococcus pneumoniae*. In particular, the present invention relates to a detection method, a detection primer set, and a detection kit, which are excellent in terms of specificity.

BACKGROUND OF THE INVENTION

*Streptococcus pneumoniae* (hereinafter abbreviated as "*S. pneumoniae*" at times) is a causative strain of pneumonia, endocarditis, bacteremia, septicemia, meningitis, and otitis media. It is important for clinical studies and diagnoses to detect infection with *S. pneumoniae* by distinguishing such *S. pneumoniae* from other alpha hemolytic streptococci, which generally coexist with the above strain in human bodies.

Selection via culture and biochemical test methods, which utilize colony form, optochin sensitivity, bile solubility, seroreaction, and the like, have conventionally been used to detect and diagnose such infection with *S. pneumoniae*.

However, when the aforementioned selection via culture is used in combination with the aforementioned biochemical test method, it takes 3 or more days until infection is determined. In addition, skilled techniques are necessary for precisely selecting its colony based on its form, a difference in color, and the like. Thus, without such skilled techniques, there has been a fear of interfering with clinical diagnosis and the subsequent treatments.

On the other hand, in recent years, a method of detecting *S. pneumoniae* using the PCR (polymerase chain reaction) method has also been proposed (Japanese Patent Application Laid-Open No. 9-327300). In the case of detection in which the PCR method is used, using primers specific to *S. pneumoniae*, nucleic acid is amplified with the collected DNA sample as a template, so as to detect the presence or absence of *S. pneumoniae* based on the presence or absence of such nucleic acid amplification. This method enables simple detection with certain reliability in a short time, when compared with the combined use of selection via culture and a biochemical test method.

DISCLOSURE OF THE INVENTION

As stated above, when *S. pneumoniae* is detected by the PCR method, it is common to carry out an amplification reaction to target a gene characteristic of *S. pneumoniae*. As such a gene characteristic of *S. pneumoniae*, a lytA gene encoding autolysin and a ply gene encoding pneumolysin have been known, for example. However, it has been recently reported that strains having genes encoding autolysin or pneumolysin exist among strains other than *S. pneumoniae*, which are classified into *Streptococcus mitis* (hereinafter abbreviated as "*S. mitis*" at times) allied to *S. pneumoniae* based on genotypes and phenotypes (refer to: Whatmore A. M., & seven other people, "Genetic relationships between clinical isolates of *Streptococcus pneumoniae*, *Streptococcus oralis*, and *Streptococcus mitis*: characterization of "atypical" pneumococci and organisms allied to *S. mitis* harboring *S. pneumoniae* virulence factor-encoding genes.", Infect. Immun., 2000, Vol. 68, pp. 1374-1382). Thus, when PCR is carried out to target a lytA gene or a ply gene as well, it has been difficult to distinguish *S. pneumoniae* from several strains such as *S. mitis* or *Streptococcus oralis* (hereinafter abbreviated to as "*S. oralis*" at times), which are resident strains in oral cavity.

Moreover, when gene amplification is carried out by the PCR method, it requires equipment such as a thermal cycler, and thus such a gene amplification method has been problematic in terms of much expense in cost and effort.

The present invention has been made to solve the aforementioned problems, and it is an object of the present invention to provide a method of rapidly and simply detecting *S. pneumoniae*, which is excellent in terms of specificity, a primer set for detecting *S. pneumoniae*, and a kit for detecting *S. pneumoniae*.

In order to develop a detection method, which is excellent in terms of specificity, so as to achieve the aforementioned object, the present inventors have first made a comparison among the nucleotide sequences of the lytA genes of 4 types of *S. pneumoniae* (GenBank Accession Nos. AE008540, AE007483, M13812, and AF467249) and the nucleotide sequences of 9 other types of strains encoding autolysin (*S. mitis* lytA genes (EMBL Accession Nos. AJ617815 and AJ617816), *Streptococcus* species lytA genes (EMBL Accession Nos. AJ252190, AJ252191, AJ252192, AJ252193, AJ252194, AJ252195, and AJ252196)). As a result, a specific nucleotide sequence only shared by *S. pneumoniae* has been clarified. Thereafter, the inventors have found that primers used in the LAMP method are designed from such nucleotide sequences, and a lytA gene is specifically amplified, so as to detect *S. pneumoniae*, thereby completing the present invention.

That is to say, the present invention includes the following features:

(1) A method of detecting *S. pneumoniae*, which is characterized in that it comprises amplifying a lytA gene derived from *S. pneumoniae* using a LAMP primer set comprising at least one primer having a nucleotide sequence that is identical to or complementary to a partial sequence in the region ranging from bp 40 to 450 of the nucleotide sequence region of the above-described lytA gene, and then detecting the obtained amplified product.

In the above-described detection method, the LAMP primer set comprising a FIP primer, a BIP primer, a F3 primer, and a B3 primer, which are designed from the region ranging from bp 40 to 450 of the nucleotide sequence of the lytA gene derived from *S. pneumoniae*, can be used, for example. In addition, such a LAMP primer set may further comprise a loop primer.

Herein, the FIP primer can be designed from the region ranging from bp 76 to 132, or from bp 239 to 308 of the nucleotide sequence of the lytA gene. The BIP primer can be designed from the region ranging from bp 153 to 216, or from bp 332 to 413 of the nucleotide sequence of the lytA gene. The F3 primer can be designed from the region ranging from bp 47 to 76, or from bp 221 to 237 of the nucleotide sequence of the lytA gene. The B3 primer can be designed from the region ranging from bp 226 to 240, or from bp 417 to 434 of the nucleotide sequence of the lytA gene. In the present invention, a loop primer may be included, and the loop primer can be designed from the region ranging from bp 178 to 195 of the nucleotide sequence of the lytA gene.

An example of a preferred primer set used in the present invention is at least one selected from the group consisting of combinations of nucleotide sequences described in the following (a) to (e):
(a) a combination of the nucleotide sequences as shown in SEQ ID NOS: 1, 2, 3, and 4;
(b) a combination of the nucleotide sequences as shown in SEQ ID NOS: 5, 2, 3, and 4;
(c) a combination of the nucleotide sequences as shown in SEQ ID NOS: 6, 7, 8, and 4;
(d) a combination of the nucleotide sequences as shown in SEQ ID NOS: 9, 10, 11, and 12; and
(e) a combination of the nucleotide sequences as shown in SEQ ID NOS: 23, 24, 15, 4, and 25.
(2) A primer set for detecting S. pneumoniae, which comprises at least one selected from the group consisting of combinations of nucleotide sequences described in the following (a) to (e):
(a) a combination of the nucleotide sequences as shown in SEQ ID NOS: 1, 2, 3, and 4;
(b) a combination of the nucleotide sequences as shown in SEQ ID NOS: 5, 2, 3, and 4;
(c) a combination of the nucleotide sequences as shown in SEQ ID NOS: 6, 7, 8, and 4;
(d) a combination of the nucleotide sequences as shown in SEQ ID NOS: 9, 10, 11, and 12; and
(e) a combination of the nucleotide sequences as shown in SEQ ID NOS: 23, 24, 15, 4, and 25.
(3) A kit for detecting S. pneumoniae, which comprises the primer set according to (2) above.

BRIEF DESCRIPTION OF THE DRAWINGS

FIG. 1 is a view showing the nucleotide sequence (SEQ ID NO: 26) of the lytA gene, and a nucleotide portion specific to S. pneumoniae and a region in which the LAMP primer of Example 1 is designed.

BEST MODES FOR CARRYING OUT THE INVENTION

Figure 2:
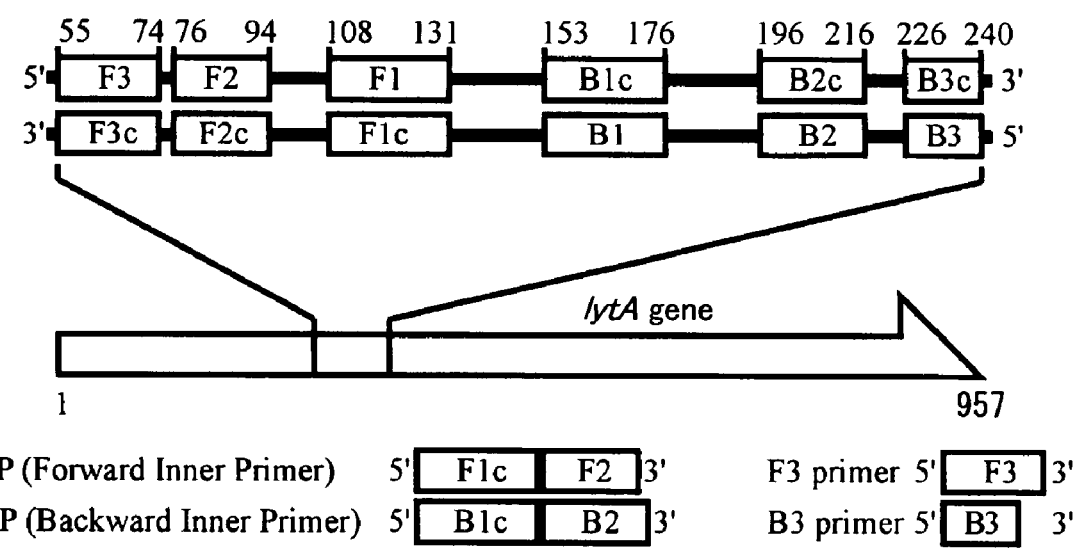
FIG. 2 is a view showing the structure of each LAMP primer of Example 1 and the position of each LAMP primer on the lytA gene.

The present invention will be described in detail below.
Publications and patent documents cited in the present specification are incorporated herein by reference in their entirety.
According to the present invention, focusing on a species-specific region in the lytA gene of S. pneumoniae, a LAMP primer set is designed, so that S. pneumoniae can be specifically detected.
The term "LAMP primer set" is used herein to mean a primer set used in nucleic acid amplification according to the loop-mediated isothermal amplification (LAMP) method (reference: Nucleic Acid Research, 2000, Vol. 28, No. 12, e63).
Since such a LAMP primer can be designed from more regions than those for a PCR primer used in the PCR method, the LAMP primer is considered to have high target selectivity Moreover, since the primer is designed from the region of the lytA gene, which is specific to S. pneumoniae, it is possible to specifically detect S. pneumoniae.
An example of the nucleotide sequence of the lytA gene (GenBank Accession No. AE008540) is shown in FIG. 1 and SEQ ID NO: 26. In FIG. 1, the line with the term "No." indicates the positions of nucleotides, and the line with the term "Primer" indicates examples of the positions of regions for designing FIP, BIP, F3 and B3 primers (as described later). In addition, the line with the term "Base" indicates the nucleotide sequence of the lytA gene in the direction of 5'→3' from the left side to the right side, just as with SEQ ID NO: 26. Moreover, the line with the term "Common part" indicates that the nucleotide with the mark "*" is common only in the aforementioned 4 types of S. pneumoniae. The arrow in each of the "primer" lines of FIG. 1 indicates the 5'→3' direction of the primer of Example 1. Accordingly, the region, the range of which is determined by the left arrow, indicates that a region complementary to the above region acts as a primer.
In the present invention, at least one type of primer has a nucleotide sequence that is identical to or complementary to at least a portion of the region ranging from bp 40 to 450. In the present invention, the entire region ranging from bp 84 to 180, in which many common nucleotides are dispersed, or the portion thereof, is preferably included in a region to be amplified (including a primer portion).
When the primer of the present invention is used in detection of S. pneumoniae, it is excellent not only in terms of specificity, but is also excellent in terms of detection sensitivity and detection promptness. Moreover, linearity is observed in an amplification curve, and quantitative capability is also favorable.
Next, the embodiments of the present invention will be described with reference to drawings.
As shown in FIG. 2, a LAMP primer set is configured by the combination of primers designed from 6 different regions on a target gene (lytA gene) (F3, F2, F1, B1c, B2c, and B3c from the 5' end side) with primers designed from regions complementary to the above regions (B3, B2, B1, F1c, F2c, and F3c from the 5' end side). The LAMP primer set used in the present invention comprises a Forward Inner Primer (hereinafter abbreviated as "FIP" at times) formed by ligating the nucleotides in the F1c region to the nucleotides in the F2 region from the 5' end side of the nucleotide sequence of the lytA gene, a Backward Inner Primer (hereinafter abbreviated as "BIP" at times) formed by ligating the nucleotides in the B1c region to the nucleotides in the B2 region from the 5' end side thereof, a F3 primer consisting of the nucleotides in the F3 region, and a B3 primer consisting of the nucleotides in the B3 region. Moreover, loop primers (Loop Primer F and/or Loop Primer B) may be further designed as desired, and DNA may be amplified using such primers, so as to detect an amplified product. The term "loop primer" is used to mean a primer having a sequence that is complementary to a single-stranded portion formed between the B1 region and the B2 region, or between the F1 region and the F2 region. In the column of Example 5 in Table 1, an example of Loop Primer B (LB) is given.

In the present invention, the FIP primer can be designed from the region ranging from bp 76 to 132 (hereinafter referred to as "76-132" at times; the same goes for other primers) of the nucleotide sequence (SEQ ID NO: 26) of the lytA gene, or from the region ranging from bp 239 to 308 thereof. For example, in Example 1, F2 is preferably designed from the region of 76-94 (F2c: the complementary strand region thereof), and F1 is preferably designed from the region of 108-131 (F1c: the complementary strand region thereof) (SEQ ID NO: 1). The BIP primer can be designed from the region of 153-216 or 332-413 of the nucleotide sequence of the lytA gene. For example, in Example 1, B1c is preferably designed from the region of 153-176 (the complementary strand of 153-176 of B1), and B2 is preferably designed from the region of 196-216 (SEQ ID NO: 2). The F3 primer can be designed from the region of 47-76 or 221-237 of the nucleotide sequence of the lytA gene. For example, in Example 1, the above primer is preferably designed from the region of 55-74 (SEQ ID NO: 3). The B3 primer can be designed from the region of 226-240 or 417-434 of the nucleotide sequence of the lytA gene. For example, in Example 1, the above primer is preferably designed from the region of 226-240 (SEQ ID NO: 4). With regard to Examples 2 to 5 also, the regions described in the columns of examples (Examples 2 to 5) in Table 1 can be selected as preferred regions used for designing the above primers.

Furthermore, the use of loop primers in the present invention enables further reduction in the time required for detection. Accordingly, either one of the loop primer F (LF) and the loop primer B (LB), or both of them, are used to promote detection.

LF can be designed from the region of 95-110 or the region of 256-283 of the nucleotide sequence of the lytA gene.

LB can be designed from the region of 176-195 of the nucleotide sequence of the lytA gene, and it can preferably be designed from the region of 178-195 (SEQ ID NO: 25).

The position in the lytA gene of the LAMP primer set of Example 1, given as an example of the present invention, is shown in FIGS. 1 and 2. The correlation between the types of primers and sequence numbers of the LAMP primer sets of Examples 1 to 5, given as examples of the present invention, is shown in Table 1.

TABLE 1

| Example/Comparative example | FIP F2 | FIP F1 | BIP B1 | BIP B2 | F3 | B3 | LB | Detection time |
|---|---|---|---|---|---|---|---|---|
| Example 1 | SEQ ID NO: 1 76-94 | 108-131 | SEQ ID NO: 2 153-176 | 196-216 | SEQ ID NO: 3 55-74 | SEQ ID NO: 4 226-240 | | 17 min 42 sec |
| Example 2 | SEQ ID NO: 5 76-94 | 106-130 | SEQ ID NO: 2 153-176 | 196-216 | SEQ ID NO: 3 55-74 | SEQ ID NO: 4 226-240 | | 33 min 2 sec |
| Example 3 | SEQ ID NO: 6 77-94 | 107-131 | SEQ ID NO: 7 153-176 | 194-215 | SEQ ID NO: 8 61-76 | SEQ ID NO: 4 226-240 | | 35 min 24 sec |
| Example 4 | SEQ ID NO: 9 239-255 | 284-308 | SEQ ID NO: 10 332-356 | 396-413 | SEQ ID NO: 11 221-237 | SEQ ID NO: 12 417-434 | | 43 min |
| Comparative example 2 | SEQ ID NO: 13 76-94 | 122-142 | SEQ ID NO: 14 155-176 | 199-218 | SEQ ID NO: 15 47-66 | SEQ ID NO: 16 235-254 | | Not-detected |
| Comparative example 3 | SEQ ID NO: 17 76-94 | 116-128 | SEQ ID NO: 18 154-175 | 199-219 | SEQ ID NO: 15 47-66 | SEQ ID NO: 19 234-254 | | Not-detected |
| Comparative example 4 | SEQ ID NO: 20 78-96 | 120-141 | SEQ ID NO: 18 154-175 | 199-219 | SEQ ID NO: 15 47-66 | SEQ ID NO: 19 234-254 | | Not-detected |
| Comparative example 5 | SEQ ID NO: 21 78-96 | 122-143 | SEQ ID NO: 14 155-176 | 199-218 | SEQ ID NO: 15 47-66 | SEQ ID NO: 16 235-254 | | Not-detected |
| Comparative example 6 | SEQ ID NO: 22 77-94 | 120-141 | SEQ ID NO: 18 154-175 | 199-219 | SEQ ID NO: 15 47-66 | SEQ ID NO: 19 234-254 | | Not-detected |
| Example 5 | SEQ ID NO: 23 76-94 | 111-132 | SEQ ID NO: 24 155-176 | 196-216 | SEQ ID NO: 15 47-66 | SEQ ID NO: 4 226-240 | SEQ ID NO: 25 178-195 | 13 min 42 sec |

With regard to the numbers described in the columns of "F2", "F1", "B1", "B2", "F3", and "B3" in Table 1, "F3", "F2", and "F1" indicate the positions in the F3 region, the F2 region, and the F1 region of the sense strand as shown in FIG. 2, respectively. On the other hand, "B1", "B2", and "B3" indicate the positions in the B1c region, the B2c region, and the B3c region of the sense strand as shown in FIG. 2, respectively. Accordingly, with regard to the FIP primer of Example 1, the region described in the "F3" column in Table 1 (the region of 108-131) means the F1c region (the complementary strand side of F1) that is a portion of the constitutional element of the FIP primer. In addition, the region described in the "B3" column in Table 1 means the B3c region of the sense strand as shown in FIG. 2. The positional numbers of such regions are applied also to other primers in the same above manner.

The nucleotide sequences of the primers as shown in Table 1 above are shown in the following Tables 2 and 3.

TABLE 2

| Example | Primer | Sequence | SEQ ID NO: |
|---|---|---|---|
| Example 1 | FIP | cgccagtgat aatccgcttc attccactca actgggaatc cgc | 1 |
|  | BIP | tttctcgcac attgttggga acggccaggc accattatca acagg | 2 |
|  | F3 | ccatataggc aagtacacgc | 3 |
|  | B3 | agcattccaa ccgcc | 4 |
| Example 2 | FIP | gccagtgata atccgcttca ttctgcactc aactgggaat ccgc | 5 |
|  | BIP | tttctcgcac attgttggga acggccaggc accattatca acagg | 2 |
|  | F3 | ccatataggc aagtacacgc | 3 |
|  | B3 | agcattccaa ccgcc | 4 |
| Example 3 | FIP | cgccagtgat aatccgcttc attctactca actgggaatc cgc | 6 |
|  | BIP | tttctcgcac attgttggga acgcaggca ccattatcaa caggtc | 7 |
|  | F3 | aggcaagtac acgcac | 8 |
|  | B3 | agcattccaa ccgcc | 4 |
| Example 4 | FIP | cggtagtccg tcatgaactc ttcttctgag acctatgcag cg | 9 |
|  | BIP | atctagcaga tgaagcaggt ttgccttcgt gcaatactcg tgc | 10 |
|  | F3 | ttggggcgg ttggaat | 11 |
|  | B3 | gagtggttgt ttggttgg | 12 |
| Example 5 | FIP | ccgccagtga taatccgctt cacactcaac tgggaatccg c | 23 |
|  | BIP | tctcgcacat tgttgggaac ggccaggcac cattatcaac agg | 24 |
|  | F3 | gcgtgcaacc atataggcaa | 15 |
|  | B3 | agcattccaa ccgcc | 4 |
|  | LB | tgcatcatgc aggtagga | 25 |

TABLE 3

| Comparative example | Primer | Sequence | SEQ ID NO: |
|---|---|---|---|
| Comparative example 2 | FIP | ctgggtcttt ccgccagtga tcactcaact gggaatccgc | 13 |
|  | BIP | tctcgcacat tgttgggaac ggtcccaggc accattatca ac | 14 |
|  | F3 | gcgtgcaacc atataggcaa | 15 |
|  | B3 | gctgcatagg tctcagcatt | 16 |
| Comparative example 3 | FIP | gtctttccgc cagtgataat ccgcactcaa ctgggaatcc gc | 17 |
|  | BIP | ttctcgcaca ttgttgggaa cggtcccagg caccattatc aac | 18 |
|  | F3 | gcgtgcaacc atataggcaa | 15 |
|  | B3 | gctgcatagg tctcagcatt c | 19 |
| Comparative example 4 | FIP | tgggtcttc cgccagtgat aactcaactg gaatccgca t | 20 |
|  | BIP | ttctcgcaca ttgttgggaa cggtcccagg caccattatc aac | 18 |
|  | F3 | gcgtgcaacc atataggcaa | 15 |
|  | B3 | gctgcatagg tctcagcatt c | 19 |
| Comparative example 5 | FIP | ctgggtcttt ccgccagtga tctcaactgg gaatccgcat | 21 |
|  | BIP | tctcgcacat tgttgggaac ggtcccaggc accattatca ac | 14 |
|  | F3 | gcgtgcaacc atataggcaa | 15 |
|  | B3 | gctgcatagg tctcagcatt | 16 |
| Comparative example 6 | FIP | tgggtcttc cgccagtgat aaactcaact gggaatccgc | 22 |
|  | BIP | ttctcgcaca ttgttgggaa cggtcccagg caccattatc aac | 18 |
|  | F3 | gcgtgcaacc atataggcaa | 15 |
|  | B3 | gctgcatagg tctcagcatt c | 19 |

The aforementioned LAMP primer set used in detection of *S. pneumoniae* can be chemically synthesized using a DNA automatic synthesizer, for example. It is to be noted that the term "primer" is used in the present invention to mean an oligonucleotide, which has a certain nucleotide sequence as described above, which is able to form a base pair with other nucleotides, and which comprises a hydroxy group acting as a base point for complementary strand synthesis at the 3' end thereof. Accordingly, as long as these conditions are satisfied, the backbone thereof is not necessarily limited to the backbone formed based on a phosphodiester bond. For example, a primer having a backbone that is not P but S, consisting of peptide nucleic acid formed based on a phosphothioate form or a peptide bond, may also be used.

The type of the template-dependent nucleic acid synthetase that can be used in the present invention is not particularly limited, as long as it has strand displacement activity. Examples of such an enzyme include Bst DNA polymerase (large fragment), Bca (exo-) DNA polymerase, Klenow fragment of *Escherichia coli* DNA polymerase I, Vent (exo-) DNA polymerase (obtained by removing exonuclease activity from Vent DNA polymerase), DeepVent (Exo-) DNA polymerase (obtained by removing exonuclease activity from DeepVent DNA polymerase), and KOD DNA polymerase. A preferred example is Bst DNA polymerase (large fragment). When such Bst DNA polymerase is used, it is preferable to carry out the reaction at a temperature between approximately 60° C. and 65° C., which is the optimal reaction temperature.

Furthermore, known techniques can be applied to detect an amplified product. For example, a labeled oligonucleotide, which specifically labels an amplified genetic sequence, is used, or the reaction solution obtained after completion of the reaction is directly subjected to agarose electrophoresis, so as to easily detect an amplified product. Still further, it is also possible to allow the primer of the present invention itself to bind to a solid phase, as in the case of a DNA chip and the like. When such a solid-phased primer is used as a synthesis initiation point, the synthetic reaction product of nucleic acid is captured by the solid phase, so that separation and detection can be easily carried out.

Still further, since gene amplification is efficiently carried out with accelerating speed according to the LAMP method, ethidium bromide, SYBR (registered trade mark) Green I, or the like, which is an intercalator specifically incorporated into a molecule of double-stranded nucleic acid, have previously been added to the reaction solution, so as to confirm amplification. Further, in the LAMP method, a large amount of substrate is consumed as a result of the synthesis of nucleic acid, and pyrophosphoric acid as a by-product reacts with magnesium that co-exists therewith, so that it becomes magnesium pyrophosphate. As a result, the reaction solution becomes clouded to such an extent that it can be confirmed by naked eyes. Such white turbidity is observed after completion of the reaction, or an increase in the turbidity during the reaction is measured using a measurement apparatus capable of optically observing such an increase in the turbidity over time. For example, a change in the absorbance at 650 nm is measured using a common spectrophotometer, so as to confirm amplification.

Various types of reagents necessary for such a LAMP reaction have previously been packaged, so that the reagents can be supplied as a kit for detecting *S. pneumoniae*. Specifically, the kit of the present invention does not only comprise the aforementioned LAMP primer set used in detection of *S. pneumoniae*, but it may also comprise dNTP used as a substrate for complementary strand synthesis, DNA polymerase used in strand displacement-type synthesis of complementary strand, a buffer solution giving preferred conditions to an enzyme reaction, and as necessary, reagents necessary for detection of the synthetic reaction product. Moreover, the above kit may further comprise a reagent for destabilizing the double strand of nucleic acid (betaine, for example).

Thus, in the LAMP method, it is possible to promote an amplification reaction only by performing isothermal incubation at a temperature in which enzyme activity can be maintained. Accordingly, differing from the PCR method, the LAMP method does not need equipment for regulation of temperature, and this method enables easy detection at low cost. At the same time, this method does not have any waste of time caused by temperature change, and thus it enables rapid detection.

EXAMPLES

The present invention will be specifically described in the following examples. However, these examples are not intended to limit the scope of the present invention.

[Concerning Specificity Confirmation Test]

The method of detecting *S. pneumoniae* of the present invention was carried out, and the specificity of the detection method of the present invention was confirmed. The specificity confirmation test will be described below.

(1) Preparation of Chromosomal DNA

First, chromosomal DNA was purified from various types of strains to be used in the test, and DNA used as a template for an amplification reaction was prepared. Chromosomal DNA was obtained by extracting such DNA from various types of strains using Dr. GenTLE (registered trade mark; manufactured by TAKARA BIO INC.) used for enzymes, and then purifying it using QIAamp (registered trade mark) DNA mini kit (manufactured by QIAGEN). Extraction and purification were carried out in accordance with the manuals included with the above kits.

In this test, chromosomal DNA was extracted from a total of 32 types of strains, which are classified into 10 *Streptococcus* species and 7 non-Streptococcus species, and was then used. These 32 types of strains are shown in Table 4.

TABLE 4

| Strain type | Example 1 | Example 2 | Example 3 | Example 4 | Example 5 |
|---|---|---|---|---|---|
| *Streptococcus mitis* ATCC903[a] | − | − | − | − | − |
| *Streptococcus oralis* ATCC9811[a] | − | − | − | − | − |
| *Streptococcus oralis* ATCC10557[a] | − | − | − | − | − |

TABLE 4-continued

| Strain type | Example 1 | Example 2 | Example 3 | Example 4 | Example 5 |
|---|---|---|---|---|---|
| *Streptococcus gordonii* ATCC12396 | − | − | − | − | − |
| *Streptococcus agalactiae* IID1625 | − | − | − | − | − |
| *Streptococcus milleri* NCTC10703 | − | − | − | − | − |
| *Streptococcus sobrinus* NIDR6715[a] | − | − | − | − | − |
| *Streptococcus sobrinus* OMZ176 | − | − | − | − | − |
| *Streptococcus mutans* XC47 | − | − | − | − | − |
| *Streptococcus mutans* PK1[a] | − | − | − | − | − |
| *Streptococcus mutans* JC2[a] | − | − | − | − | − |
| *Streptococcus sanguinis* ATCC10556[a] | − | − | − | − | − |
| *Streptococcus salivarius* ATCC7073[a] | − | − | − | − | − |
| *Streptococcus salivarius* ATCC9222[a] | − | − | − | − | − |
| *Streptococcus salivarius* HHT[a] | − | − | − | − | − |
| *Streptococcus pneumoniae* R6 | + | + | + | + | + |
| *Streptococcus pneumoniae* ATCC6305 | + | + | + | + | + |
| *Streptococcus pneumoniae* GTC261 (NCTC7465)[b] | + | + | + | + | + |
| *Streptococcus pneumoniae* IID553 (NYSDH DP-2)[c] | + | + | + | + | + |
| *Streptococcus pneumoniae* IID554 (NYSDH DP-3, 5A)[c] | + | + | + | + | + |
| *Haemophilus influenzae* RD | − | − | − | − | − |
| *Escherichia coli* DH5α | − | − | − | − | − |
| *Actinobacillus actinomycetemcomitans* Y-4 | − | − | − | − | − |
| *Porphyromonas gingivalis* ATCC33277 | − | − | − | − | − |
| *Porphyromonas gingivalis* 381[a] | − | − | − | − | − |
| *Porphyromonas gingivalis* ATCC49417[a] | − | − | − | − | − |
| *Actinomyces naeslundii* ATCC12104[a] | − | − | − | − | − |
| *Actinomyces naeslundii* T14[a] | − | − | − | − | − |
| *Actinomyces naeslundii* WVU627[a] | − | − | − | − | − |
| *Prevotella intermedia* ATCC25611[a] | − | − | − | − | − |
| *Prevotella nigrescens* ATCC25261[a] | − | − | − | − | − |
| *Prevotella nigrescens* ATCC33563[a] | − | − | − | − | − |

In the above table, the superscript notation a indicates that the strain had been obtained from Department of Microbiology, Nihon University School of Dentisrty.
In the above table, the superscript notation b indicates that the strain had been obtained from Department of Microbiology, Gifu University School of Medicine.
In the above table, the superscript notation c indicates that the strain had been obtained from the Institute of Medical Science, the University of Tokyo.

(2) Concerning LAMP Reaction

Next, using the LAMP primer sets of Examples 1 to 5 (refer to Table 1), a LAMP reaction was carried out with the chromosomal DNA derived from various types of strains prepared in (1) above as a template.

A LAMP reaction solution (25 µl) was prepared by mixing 40 pmol each of FIP and BIP, 5 pmol each of the F3 primer and the B3 primer, 8 U of Bst DNA polymerase large fragment (manufactured by New England Biolabs), deoxynucleoside triphosphate (1.4 mM each), betaine (0.8 M), Tris-HCl buffer (20 mM; pH 8.8), KCl (10 mM), $(NH_4)_2SO_4$ (10 mM), $MgSO_4$ (8 mM), 0.1% Tween 20, and 2 µl of the template DNA solution prepared as described in (1) above.

Thereafter, the LAMP reaction solution was incubated at 63° C. for 35 minutes or 60 minutes, so as to promote the LAMP reaction. Finally, the reaction solution was heated at 80° C. for 2 minutes, so as to terminate the reaction.

(3) Concerning Confirmation of Presence or Absence of Amplification

The presence or absence of amplification was detected by directly looking at the reaction tube by eyes, and observing the presence or absence of white turbidity of the LAMP reaction solution. That is to say, when a replication sequence exists, magnesium pyrophosphate is generated as a by-product of the reaction in an amount that is proportional to the amount of the replication sequence, and the LAMP reaction solution thereby becomes clouded. On the other hand, when such a replication sequence does not exist, the LAMP reaction solution remains transparent. Thus, the degree of such white turbidity was used as an index for detection of an amplified product.

Moreover, the presence or absence of amplification was also confirmed by agarose gel electrophoresis performed on the amplified product. At the time, each of the amplified product itself and the product obtained by digestion of the amplified product with the restriction enzyme TasI (manufactured by Fermentas) was electrophoresed in 3% agarose gel. Thereafter, the resultant was stained with ethidium bromide, so as to confirm the electrophoretic pattern. When the amplified product is directly electrophoresed, the replication sequence appears as a ladder pattern that is characteristic of the LAMP reaction. When the product obtained by digestion of the amplified product with the restriction enzyme is electrophoresed, the replication sequence appears in the form of fragments having a size of 102 bp or 111 bp.

(4) Concerning Test Results

The results of the aforementioned test are shown in Table 4. With regard to the results, "+" indicates a case where amplification (white turbidity) was confirmed by visual observation after completion of the incubation for 35 minutes or 60 minutes, and "−" indicates a case where such amplification was not confirmed by visual observation after completion of the incubation for 60 minutes. As a result, as shown in Table 4, even if any one of the LAMP primer sets of Examples 1 to 5 was used, when *S. pneumoniae* was used as a template, a large amount of amplified product was confirmed after completion of the incubation for 35 minutes or 60 minutes. In contrast, in the case of all other strains, after completion of the incubation for 60 minutes, no amplified products were confirmed. Such results corresponded to the results of electrophoresis. In Example 1, fragments of 102 bp and 111 bp were confirmed. Moreover, the amplified product was also sequenced. As a result, the sequence amplified as a result of the LAMP reaction matched with an anticipated sequence.

From these results, it was confirmed that the method of detecting *S. pneumoniae* of the present invention is excellent in terms of specificity.

[Concerning Sensitivity Confirmation Test]

Next, detection sensitivity obtained using each of the primer sets of the aforementioned Examples 1 to 5 was confirmed. Such detection sensitivity will be described below.

(1) Preparation of Chromosomal DNA

In the present test, as in the case of the specificity confirmation test, chromosomal DNA was purified from *S. pneumoniae* ATCC6305, and it was then used as a template. The template DNA concentration (copy number) in the reaction solution was assayed, at a molecular size of 2 Mbp, using Ultrospec 3300 pro (manufactured by Amersham Biosciences).

(2) LAMP Method and PCR Method

The template DNA solution, which had previously been assayed as described in (1) above, was diluted at a stepwise of every 10 times, so as to prepare a solution that was diluted by a factor between 1 and 1,000,000. Using this solution as a template DNA solution for the LAMP reaction, a detection limit was confirmed. It is to be noted that the LAMP reaction solution was the same as that used in the aforementioned specificity confirmation test in terms of the additive amount of the template DNA solution and the additive amounts of other additives, with the exception that the concentration of the template DNA solution was different. Conditions for the LAMP reaction were also the same as those applied to the aforementioned specificity confirmation test.

Moreover, in order to compare with the detection method of the present invention, amplification and detection were carried out also by the PCR method (Comparative example 1).

As a PCR primer set, a primer set (lytA-F and lytA-R) targeting a gene encoding autolysin (lytA gene) was used (Nagai, K. & 6 other people, "Evaluation of PCR primers to screen for *Streptococcus pneumoniae* isolates and β-lactam resistance, and to detect common macrolide resistance determinants," J. Antimicrob. Chemoth., 2001, Vol. 48, pp. 915-918). The sequences thereof are shown below.

```
lytA-F:  caaccgtaca gaatgaagcg g   (SEQ ID NO: 27)

lytA-R:  ttattcgtgc aatactcgtg cg  (SEQ ID NO: 28)
```

The PCR reaction solution (10 μl) was prepared by mixing deoxynucleoside triphosphate (0.2 mM each), Tris-HCl buffer (10 mM; pH 8.3), KCl (50 mM), $MgCl_2$ (2 mM), 1 U ExTaq DNA polymerase (manufactured by TAKARA BIO INC.), the forward primer (lytA-F) and the reverse primer (lytA-R) (each 0.5 mM), and 1 μl of a template DNA solution.

The PCR reaction was carried out for 30 cycles using Thermal Cycler (manufactured by MJ Research). In each cycle, denaturation at 94° C. for 15 seconds, annealing at 53° C. for 15 seconds, and synthesis at 72° C. for 15 seconds were successively carried out.

(3) Concerning Confirmation of Presence or Absence of Amplification

The presence or absence of amplification as a result of the LAMP reaction was determined by confirming white turbidity by visual observation, as with the aforementioned specificity confirmation test.

Thereafter, both the presence or absence of amplification as a result of the LAMP reaction, and the presence or absence of an amplified product by PCR in Comparative example 1, were also confirmed by subjecting the amplified product (2 μl) to 3% agarose gel electrophoresis.

(4) Concerning Test Results

With regard to the test results, "+" indicates a case where an amplified product was confirmed by electrophoresis as described above, and "−" indicates a case where such amplification was not confirmed. The test results are shown in Table 5 and FIG. 3.

TABLE 5

| | Template DNA concentration (copy number) | | | | | | | |
|---|---|---|---|---|---|---|---|---|
| | 1,000,000 | 100,000 | 10,000 | 1,000 | 100 | 10 | 1 | 0 |
| Example 1 (35 min) | + | + | + | + | − | − | − | − |
| Example 1 (60 min) | + | + | + | + | + | + | − | − |
| Example 2 (35 min) | + | − | − | − | − | − | − | − |
| Example 2 (60 min) | + | + | + | + | − | − | − | − |
| Example 3 (35 min) | − | − | − | − | − | − | − | − |
| Example 3 (60 min) | + | + | + | + | − | − | − | − |
| Example 4 (35 min) | − | − | − | − | − | − | − | − |
| Example 4 (60 min) | + | + | − | − | − | − | − | − |
| Example 5 (35 min) | + | + | + | + | + | − | − | − |
| Example 5 (60 min) | + | + | + | + | + | + | − | − |
| Comparative example 1 (PCR) | + | + | + | − | − | − | − | − |

As shown in Table 5, in the detection method using the LAMP primers of Example 1, an amplified product could be detected by carrying out the LAMP reaction for 60 minutes, even in a case where the concentration of template DNA was 10 copies. In addition, in the case of the detection method using the LAMP primers of Example 5, an amplified product could be detected by carrying out the LAMP reaction for only 35 minutes, in a case where the concentration of template DNA was 10 copies. On the other hand, in the case of detection using the PCR method, 10,000 copies were necessary as a template DNA concentration to detect an amplified product. Thus, it was confirmed that the detection sensitivity of Examples 1 and 5, in which the LAMP reaction was used, was 1,000 times greater than that of Comparative example 1. Moreover, as shown in Table 5, when the template DNA concentration was 1,000 copies, it took 35 minutes to detect an amplified product in Examples 1 and 5, and it took 60 minutes to detect it in Examples 2 and 3. Thus, it was confirmed that the above detection methods were excellent in terms of sensitivity and promptness.

Figure 3:
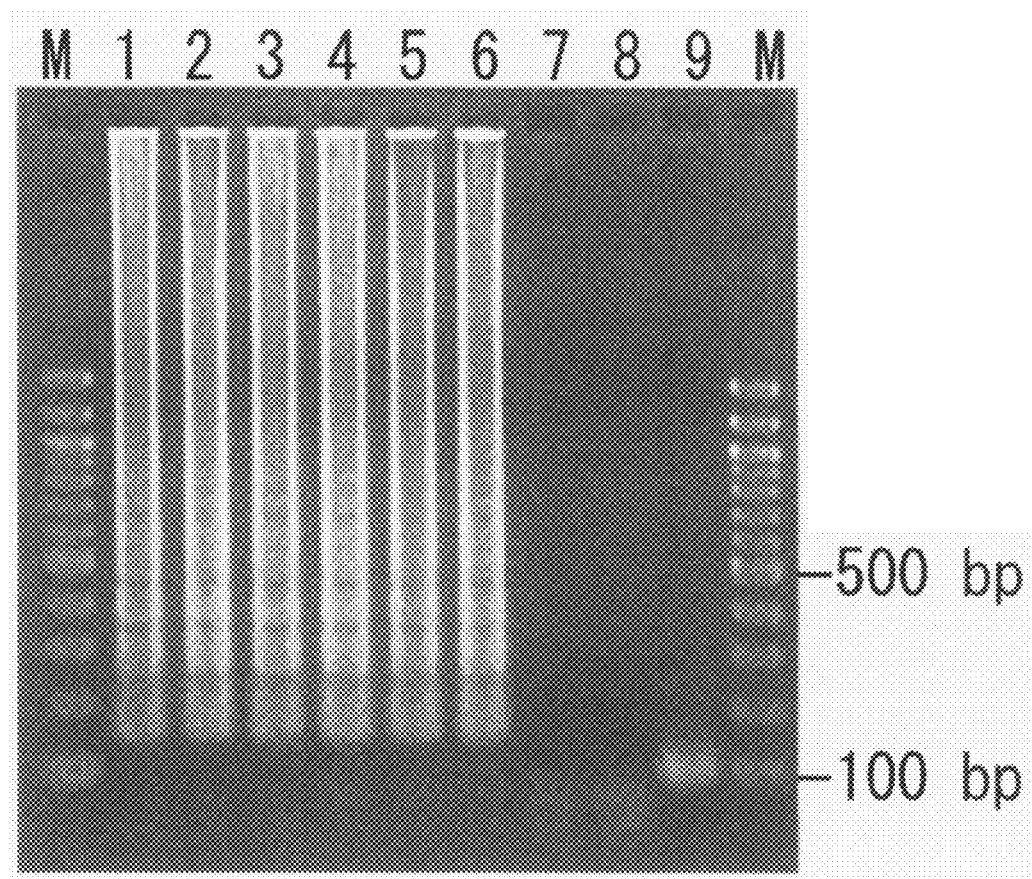
FIG. 3 is a photograph showing the results of electrophoresis performed in a sensitivity test.

FIG. 3 shows a photograph of the gel, on which the amplified product obtained after the LAMP reaction was electrophoresed. Lane M on both sides of the paper is a lane obtained by feeding a marker for indicating intervals of 100 bp. Lane 1 is a lane obtained by feeding an amplified product obtained when the template DNA concentration was set at 1,000,000 copies, lane 2 is a lane obtained by feeding an amplified product obtained when the template DNA concentration was set at 100,000 copies, and lane 3 is a lane obtained by feeding an amplified product obtained when the template DNA concentration was set at 10,000 copies. Lane 4 is a lane obtained by feeding an amplified product obtained when the template DNA concentration was set at 1,000 copies, lane 5 is a lane obtained by feeding an amplified product obtained when the template DNA concentration was set at 100 copies, and lane 6 is a lane obtained by feeding an amplified product obtained when the template DNA concentration was set at 10 copies. Lane 7 is a lane obtained by feeding an amplified product obtained when the template DNA concentration was set at 1 copy, and lane 8 is a lane obtained by feeding an amplified product obtained when the template DNA concentration was set at 0 copy.

Moreover, lane 9 is a lane obtained by digesting the amplified product of lane 1 with TasI and then electrophoresing the digest. Since the TasI site exists around the center of the target site (between F1 and B1c), when the amplified product is treated with TasI, it is cleaved around the center of the target site (between F1 and B1c), so that it can be fragmented into the length between loops. Thus, it is predicted that bands appear at positions of 102 bp and 111 bp in the case of lane 9.

In lanes 1 to 6, the amplified product had a ladder electrophoretic pattern. It was thereby confirmed that the amplified product had an inversed portion, and that it adopted a stem-loop structure characteristic of the LAMP reaction. In addition, the sections appeared at 102 bp and 111 bp in lane 9, and thus it was confirmed that a portion to be targeted had been amplified.

[Concerning Clinical Detection]

Next, clinical detection was carried out using the LAMP primer sets of Examples 1 to 5. Such clinical detection will be described below.

First, a sample was collected from the oral mucosa of a healthy child (5 to 6 years old), and 25 alpha hemolytic *streptococcus* species having a gene encoding pneumolysin or autolysin were then isolated from the sample by the PCR method. The same primer set as that used in the aforementioned sensitivity test was used as a PCR primer set targeting such a gene encoding autolysin. In addition, as a PCR primer set targeting such a gene encoding pneumolysin, the following PCR primer set (ply-F and ply-R) was used (Salo, P. & two other people, "Diagnosis of bacteremic pneumococcal pneumonia by amplification of pneumolysin gene fragment in serum", J. Infect. Dis., Vol. 171, pp. 479-482). The nucleotide sequences of the above primers are shown below.

```
ply-F: atttctgtaa cagctaccaa cga   (SEQ ID NO: 29)
ply-R: gaattccctg tcttttcaaa gtc   (SEQ ID NO: 30)
```

Moreover, in the case of the PCR reaction targeting a gene encoding autolysin, the composition of the PCR reaction solution and conditions for the PCR reaction were the same as those applied to the aforementioned sensitivity test. On the other hand, in the case of the PCR reaction targeting a gene encoding pneumolysin, the composition of the reaction solution was the same as that applied to the aforementioned sensitivity test. However, as for reaction conditions, the reaction was carried out for 30 cycles using Thermal Cycler (manufactured by MJ Research). In each cycle, denaturation at 94° C. for 1 minute, annealing at 55° C. for 1 minute, and synthesis at 72° C. for 1 minute were successively carried out.

Such 25 isolated alpha hemolytic *streptococcus* species were classified into 4 types of *S. pneumoniae* and 21 types of cell strains belonging to *Streptococcus* species, which have a gene encoding pneumolysin or autolysin as a pathogenic factor generally observed in *Diplococcus pneumoniae* (namely, 3 types of *S. oralis*, 17 types of *S. mitis*, and 1 type of unidentified cell strain belonging to *Streptococcus* species). The isolated strains are shown in Table 6.

TABLE 6

| Isolation No. | Identification according to API | Optochin sensitivity | Bile solubility | Identification results by criteria (1) to (3) | PCR lytA | PCR ply | Example 1 | 2 | 3 | 4 | 5 |
|---|---|---|---|---|---|---|---|---|---|---|---|
| 1 | S. oralis | − | + | S. oralis | − | + | − | − | − | − | − |
| 2 | S. mitis | − | + | S. mitis | + | − | − | − | − | − | − |
| 3 | S. mitis | − | + | S. mitis | − | + | − | − | − | − | − |
| 4 | S. mitis | − | + | S. mitis | − | + | − | − | − | − | − |
| 5 | S. mitis | − | + | S. mitis | − | + | − | − | − | − | − |
| 6 | S. oralis | − | + | S. oralis | − | + | − | − | − | − | − |
| 7 | S. mitis | − | + | S. mitis | − | + | − | − | − | − | − |
| 8 | S. mitis | − | + | S. mitis | − | + | − | − | − | − | − |
| 9 | S. mitis | − | + | S. mitis | − | + | − | − | − | − | − |
| 10 | S. mitis | − | − | S. mitis | − | + | − | − | − | − | − |
| 11 | S. mitis | − | − | S. mitis | − | + | − | − | − | − | − |
| 12 | S. pneumoniae | + | + | S. pneumoniae | + | + | + | + | + | + | + |
| 13 | S. pneumoniae | + | + | S. pneumoniae | + | + | + | + | + | + | + |
| 14 | S. pneumoniae | + | + | S. pneumoniae | + | + | + | + | + | + | + |
| 15 | not identified | − | − | S. species | + | − | − | − | − | − | − |
| 16 | S. mitis | − | − | S. mitis | − | + | − | − | − | − | − |
| 17 | S. mitis | − | + | S. mitis | − | + | − | − | − | − | − |
| 18 | S. oralis | − | − | S. oralis | − | + | − | − | − | − | − |
| 19 | S. pneumoniae | + | + | S. pneumoniae | + | + | + | + | + | + | + |
| 20 | S. mitis | − | − | S. mitis | + | − | − | − | − | − | − |
| 21 | S. mitis | − | + | S. mitis | − | + | − | − | − | − | − |
| 22 | S. mitis | − | + | S. mitis | − | + | − | − | − | − | − |

TABLE 6-continued

| Isolation No. | Identification according to API | Optochin sensitivity | Bile solubility | Identification results by criteria (1) to (3) | PCR lytA | PCR ply | Example 1 | Example 2 | Example 3 | Example 4 | Example 5 |
|---|---|---|---|---|---|---|---|---|---|---|---|
| 23 | S. mitis | − | + | S. mitis | − | + | − | − | − | − | − |
| 24 | S. mitis | − | + | S. mitis | − | + | − | − | − | − | − |
| 25 | S. mitis | − | − | S. mitis | + | − | − | − | − | − | − |

Next, the aforementioned 25 types of strains were identified according to the following criteria (1) to (3) generally applied to streptococci existing in oral cavity.
(1) An optochin sensitivity test was carried out in the presence of 5% $CO_2$, using a disk having a diameter of 6.5 mm and containing 5 μg of optochin (manufactured by Eiken Chemical Co., Ltd.). When an inhibition ring having a diameter of at least 13 mm was not formed, it was determined as "absence of sensitivity," and it was expressed as "−." In contrast, when an inhibition ring having a diameter of at least 13 mm was formed, it was determined as "presence of sensitivity," and it was expressed as "+".
(2) A bile solubility test was carried out according to the method of Hawn and Beebe (refer to: Hawn C. V. Z., E. Beebe., "Rapid method for demonstrating bile solubility of *Diplococcus pneumoniae*.", J. Bacteriol., 1965, Vol. 90, p. 549). In the case of bile solubility, it was expressed as "+," and in the case of bile insolubility, it was expressed as "−".
(3) Identification was carried out based on enzyme activity, sugar fermentation, and the like, using a commercially available kit, API20 Strep (manufactured by bioMerieux).

The results of the aforementioned criteria (1) to (3), and identification results obtained by comprehensively determining from criteria (1) to (3), are shown in Table 6.

Moreover, using the PCR method and the LAMP method, the 25 types of strains were screened. At the time, in order to compare the PCR method with the LAMP method, the template DNA copy number was adjusted to be 106 copies per reaction tube. The aforementioned PCR primers were used, whereas the primers of Examples 1 to 5 were used as LAMP primers. The reaction time in the LAMP method was set at 60 minutes.

As a result, in the LAMP method, 4 types of strains (*S. pneumoniae*) exhibited a positive reaction, and 21 types of strains exhibited a negative reaction. In contrast, in the PCR method, regarding the lytA gene, 8 types of strains exhibited a positive reaction, and 17 types of strains exhibited a negative reaction. Furthermore, regarding the ply gene, 21 types of strains exhibited a positive reaction, and 4 types of strains exhibited a negative reaction.

Hence, when the LAMP method was applied, 4 types of *S. pneumoniae* were perfectly detected without detecting other 21 types of strains. In contrast, when the PCR method was applied, 4 types of strains were incorrectly detected as positive regarding the lytA gene, and 17 types of strains were incorrectly detected regarding the ply gene.

Therefore, according to the detection method of the present invention, it is possible to distinguish *S. pneumoniae* from *S. mitis* and *S. oralis* allied to *S. pneumoniae*, which live together with *S. pneumoniae* in oropharynx, and the sequence of 16SrRNA of which is 99% or more identical to that of *S. pneumoniae*. Thus, it was confirmed that the present detection method is effective for the clinical diagnosis of infection with *S. pneumoniae*.

[Concerning Real-Time Turbidity Measurement Test]
Next, real-time turbidity measurement was performed on the LAMP reaction using the LAMP primer sets of Examples 1, 2, and 4 (the sequences are shown in Table 2).
(1) Concerning Detection Promptness
In the present test, the LAMP primer sets of Examples 1, 2, and 4 were used, and the composition of the LAMP reaction solution and conditions for the LAMP reaction were determined to be the same as those as described above. The template DNA concentration (copy number) was adjusted to be a certain copy number per reaction tube, and the LAMP reaction was then carried out for 60 minutes. During the LAMP reaction, using Loopamp (registered trade mark) real-time turbidity measurement apparatus (manufactured by TERAMECS Co., Ltd.; model: LA-200), the absorbance at 650 nm was read out every 6 seconds.

Figure 4:
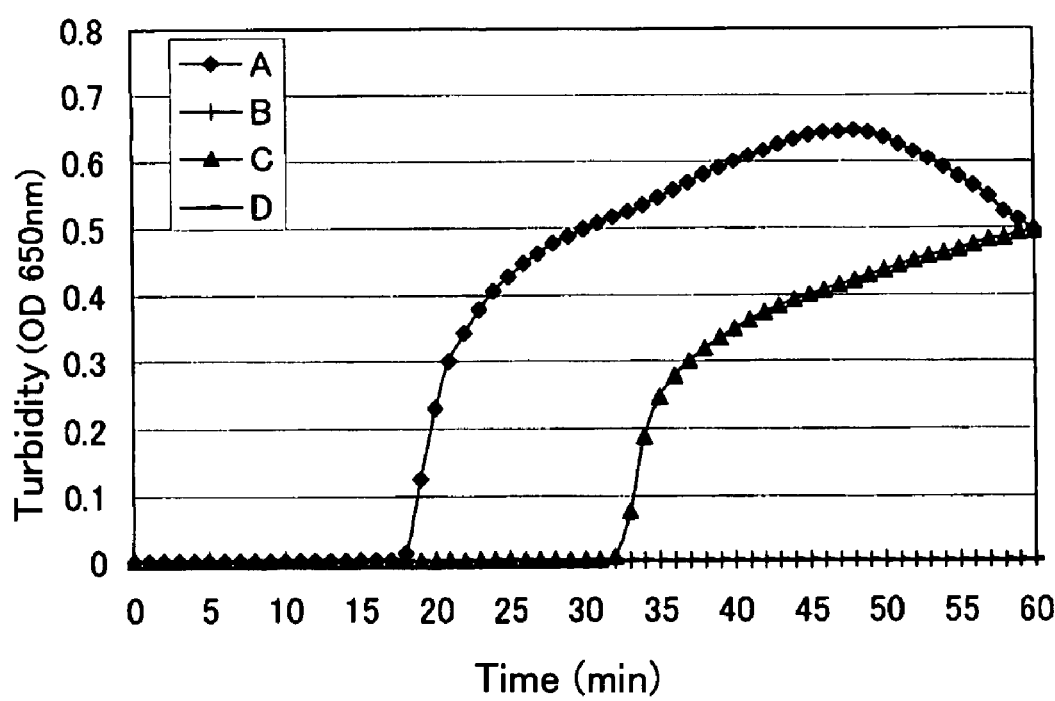
FIG. 4 is a graph showing the results of the real-time turbidity measurement (comparison between Examples 1 and 2).
Figure 5:
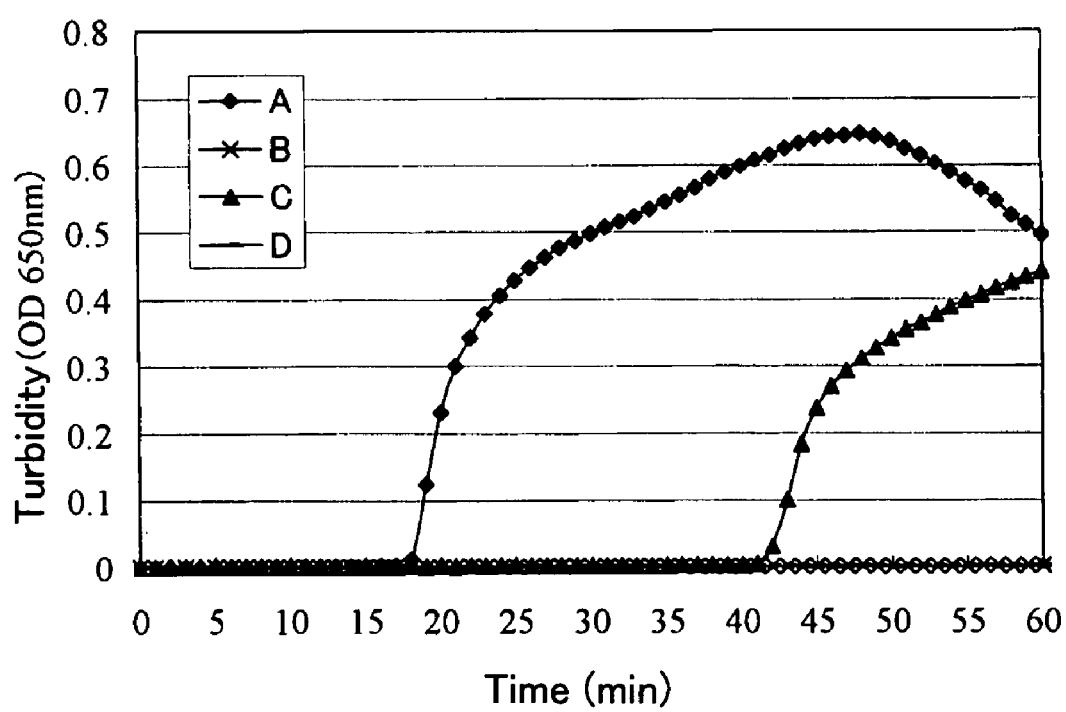
FIG. 5 is a graph showing the results of the real-time turbidity measurement (comparison between Examples 1 and 4).

The results are shown in FIGS. 4 and 5. In FIG. 4, A represents amplification results obtained using the primers of Example 1 and using DNA with a copy number of $10^7$ as a template; B represents amplification results obtained using the primers of Example 1 and using DNA with a copy number of 0 as a template; C represents amplification results obtained using the primers of Example 2 and using DNA with a copy number of $10^7$ as a template; and D represents amplification results obtained using the primers of Example 2 and using DNA with a copy number of 0 as a template. In FIG. 5, A represents amplification results obtained using the primers of Example 1 and using DNA with a copy number of $10^7$ as a template; B represents amplification results obtained using the primers of Example 1 and using DNA with a copy number of 0 as a template; C represents amplification results obtained using the primers of Example 4 and using DNA with a copy number of $10^7$ as a template; and D represents amplification results obtained using the primers of Example 4 and using DNA with a copy number of 0 as a template.

As shown in these figures, even if the template DNA concentration was the same, the time in which turbidity appeared (amplification efficiency) was different depending on the types of the LAMP primers. However, it was confirmed that detection could be carried out in any of the examples, and that detection could be carried out most rapidly in the case of using the LAMP primer set of Example 1. In particular, there was only a slight difference in sequences between the primer set of Example 1 and the primer set of Example 2 (one nucleotide at the 5' end in the F1c region of FIP and two nucleotides at the 3' end thereof), and both primer sets were almost the same in terms of performance such as specificity or sensitivity.

The promptness of detection is different due to a slight difference in the F1c region. It is considered that this is because the above F1c region that forms an elongation reaction origin (loop portion) characteristic of the LAMP reaction plays an important role in determination of the LAMP reaction rate. In particular, from the test results of Examples 1 and 2, it is assumed that C (bp 131 on the lytA gene) that is adjacent to 3 nucleotides specific to *S. pneumoniae* plays an important role for the promptness of F1c/F1 annealing in formation of the loop portion on the 5' end side of the F1c region.

Subsequently, the template DNA concentration was adjusted to be 0 to $10^6$ per reaction tube. The LAMP primer set of each of Examples 1 and 4 was added thereto, and the LAMP reaction was then carried out. During the reaction, using the aforementioned real-time turbidity measurement apparatus, the absorbance at 650 nm was measured every 6 seconds.

Figure 6:
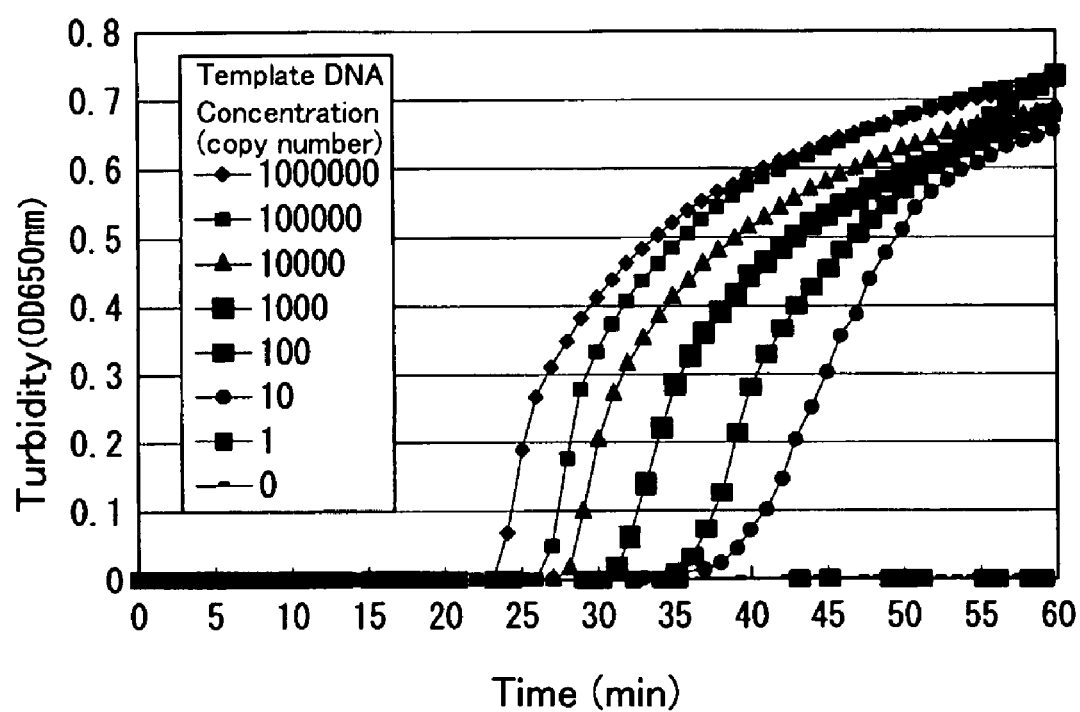
FIG. 6 is a graph showing the measurement results of the real-time turbidity of Example 1.

The results of the real-time turbidity measurement in Example 1 are shown in FIG. 6.

As shown in FIG. 6, it was confirmed that when the concentration of template DNA is 10 copies or greater, the turbidity becomes 0.1 or greater within 60 minutes. Such results correspond to the results regarding the presence or absence of amplification obtained by visual observation and electrophoresis in the aforementioned sensitivity test. Moreover, it was confirmed that as the concentration of the initially used template DNA increases, the threshold time (time required until the turbidity exceeds 0.1) becomes shorter.

Figure 7:
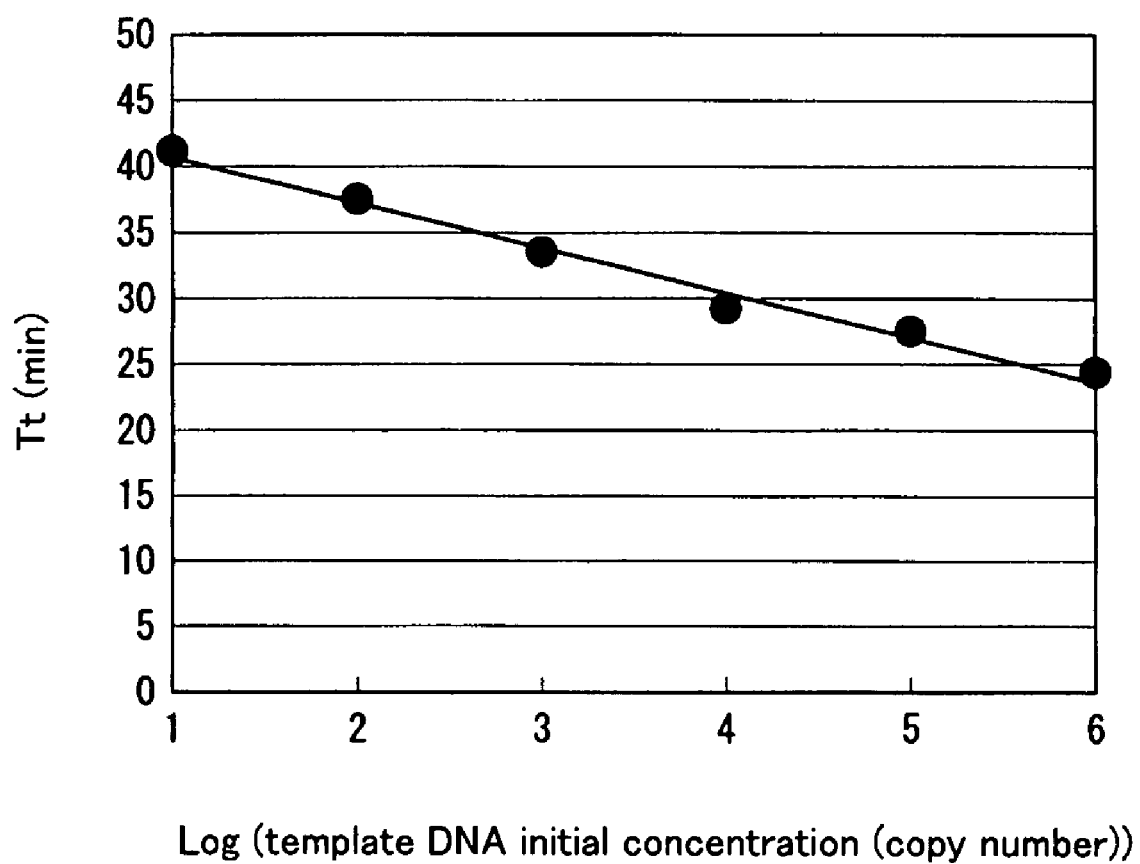
FIG. 7 is a graph showing the relationship between turbidity and the common logarithm of a template DNA concentration.

FIG. 7 shows the relationship between the threshold time (Tt) in the case of Example 1 and the common logarithm of the initial template DNA concentration. Linearity was observed between such two factors, and a high correlation (correlation coefficient $r^2=0.986$) was obtained. As Mori et al. have reported in 2004, this means that when the initial concentration of template DNA derived from *S. pneumoniae* is unknown, not only the presence or absence of the DNA, but also the concentration thereof can be assayed (Mori, Y. & three other people, "Real-time turbidimetry of LAMP reaction for quantifying template DNA," J. Biochem. Biophys. Methods, Vol. 59, pp. 145-157). That is to say, for example, even regarding a sample whose concentration is unknown, diluted solutions having different dilution ratios are prepared, and the LAMP reaction is carried out using each diluted solution. Thereafter, the threshold time is measured, so as to produce a regression line. Thus, from the regression line, the initial concentration of template DNA, which has been unknown, can be determined.

Figure 8:
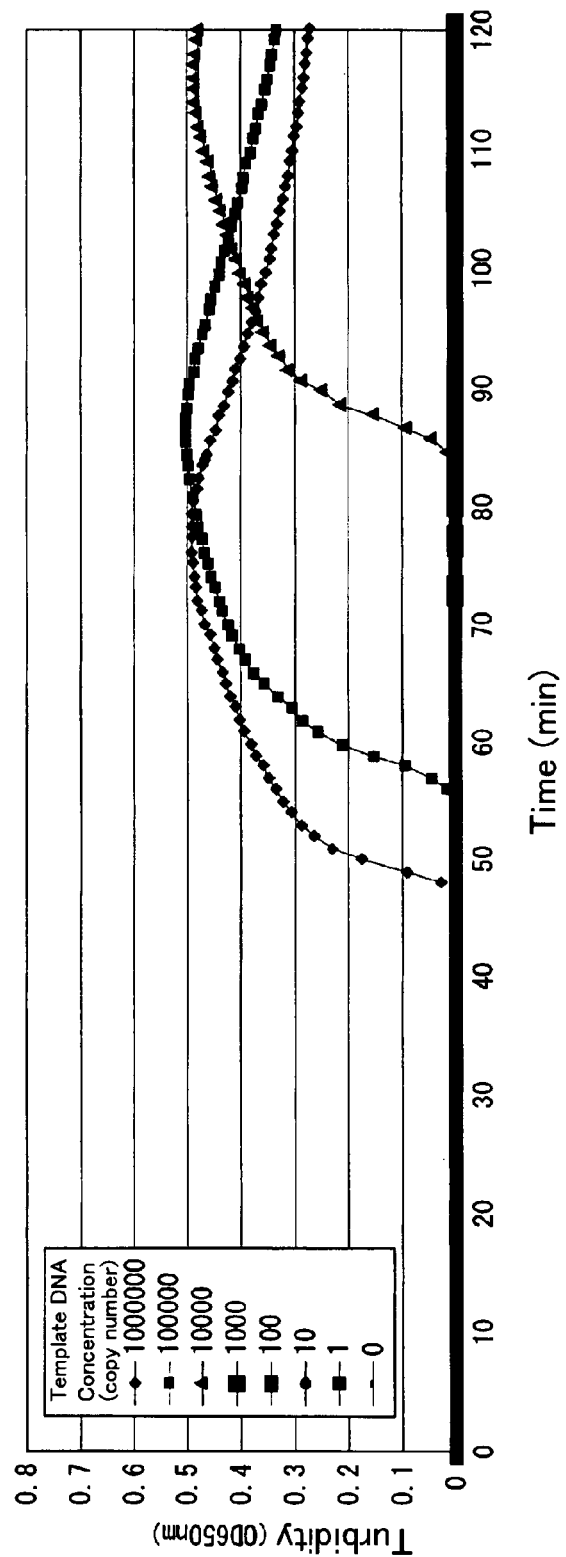
FIG. 8 is a graph showing the measurement results of the real-time turbidity of Example 4.

When the LAMP primer set of Example 4 was used, the rising curves of turbidity were depicted as shown in FIG. 8. The threshold time of 10,000 copies was approximately 85 minutes, but it was sufficiently detected (FIG. 8). In addition, as shown in FIG. 8, it was confirmed that the threshold times of the obtained 3 samples had a correlation to a small extent.

As stated above, *S. pneumoniae* could be detected in each example. Among others, the primer set of Example 1 was extremely excellent in terms of detection promptness and quantitative capability.

[Detection by LAMP Method Using Loop Primer]

Chromosomal DNA was prepared in the same manner as described above. The primers described in the "Example 5" column of Table 1 (SEQ ID NOS: 23, 24, 15, 4, and 25) were used as a LAMP primer set, and a LAMP reaction was carried out using the chromosomal DNA as a template.

Figure 9:
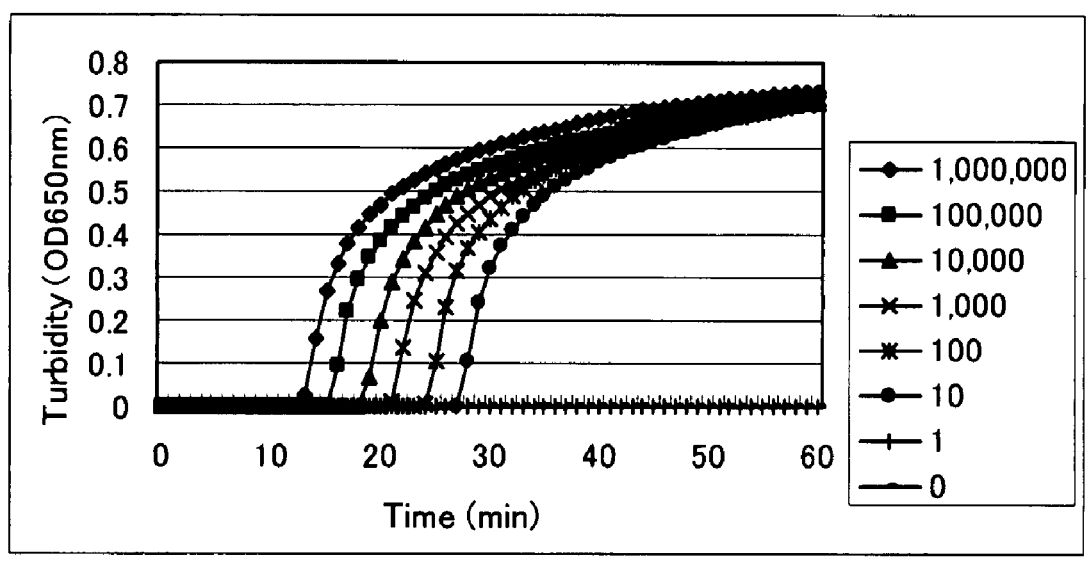
FIG. 9 is a graph showing the measurement results of the real-time turbidity of Example 5.
Figure 10:
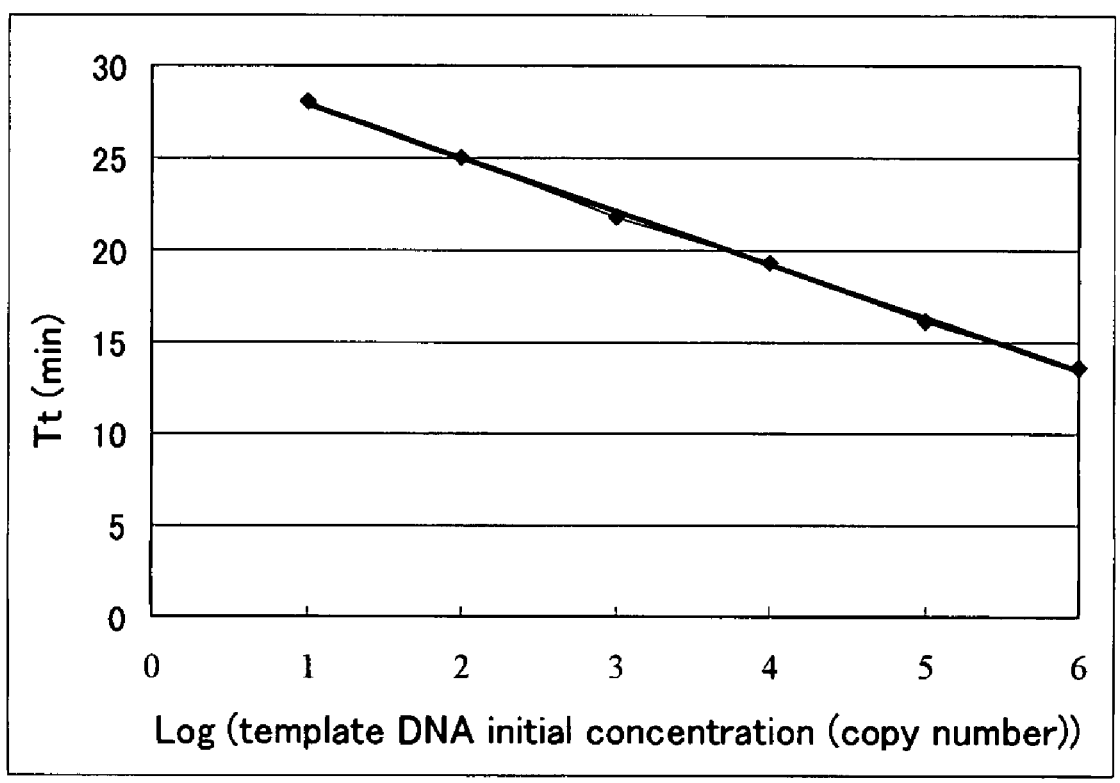
FIG. 10 is a graph showing the relationship between threshold time and the common logarithm of a template DNA copy number of Example 5.

The results are shown in Table 1 and FIGS. 9 and 10.

When a loop primer was used, the time required for detection was 13 minutes 42 seconds (Table 1), and thus detection could be carried out more rapidly than in Example 1.

FIG. 9 is a graph showing the measurement results of the LAMP reaction rate, which was measured using a real-time turbidity measurement apparatus. As shown in FIG. 9, it was confirmed that when the template DNA concentration was 10 or more copies, the turbidity became 0.1 or greater within 30 minutes. As the template DNA concentration increased from 10 copies to $10^6$ copies every 10 times, the threshold time was reduced.

FIG. 10 shows the relationship between the reaction time and the DNA concentration. Both factors showed a linear relationship having an $r^2$ value of 0.999.

INDUSTRIAL APPLICABILITY

The present invention has specificity that is superior to the conventional PCR method or the like, and also has high detection sensitivity. The above detection method enables rapid detection, and also enables quantification of *S. pneumoniae*. In addition, since the LAMP reaction progresses even under isothermal conditions and the results can be confirmed by visual observation, it requires simple equipment, and thus it can be simply and rapidly carried out even in an examination room in hospital and the like.

Sequence Listing Free Text
SEQ ID NO: 1 Synthetic DNA
SEQ ID NO: 2 Synthetic DNA
SEQ ID NO: 3 Synthetic DNA
SEQ ID NO: 4 Synthetic DNA
SEQ ID NO: 5 Synthetic DNA
SEQ ID NO: 6 Synthetic DNA
SEQ ID NO: 7 Synthetic DNA
SEQ ID NO: 8 Synthetic DNA
SEQ ID NO: 9 Synthetic DNA
SEQ ID NO: 10 Synthetic DNA
SEQ ID NO: 11 Synthetic DNA
SEQ ID NO: 12 Synthetic DNA
SEQ ID NO: 13 Synthetic DNA
SEQ ID NO: 14 Synthetic DNA
SEQ ID NO: 15 Synthetic DNA
SEQ ID NO: 16 Synthetic DNA
SEQ ID NO: 17 Synthetic DNA
SEQ ID NO: 18 Synthetic DNA
SEQ ID NO: 19 Synthetic DNA
SEQ ID NO: 20 Synthetic DNA
SEQ ID NO: 21 Synthetic DNA
SEQ ID NO: 22 Synthetic DNA
SEQ ID NO: 23 Synthetic DNA
SEQ ID NO: 24 Synthetic DNA
SEQ ID NO: 25 Synthetic DNA
SEQ ID NO: 26 Synthetic DNA
SEQ ID NO: 27 Synthetic DNA
SEQ ID NO: 28 Synthetic DNA
SEQ ID NO: 29 Synthetic DNA
SEQ ID NO: 30 Synthetic DNA

What is claimed is:

1. A method of detecting *Streptococcus pneumoniae* comprising:

amplifying by isothermal amplification at least a portion of a lytA gene derived from *Streptococcus pneumoniae* using a loop-mediated isothermal amplification (LAMP) primer set, wherein the primer set is at least one selected from the group consisting of combinations of nucleotide sequences described in the following (a) to (e):

(a) a combination of the nucleotide sequences as shown in SEQ ID NOS: 1, 2, 3, and 4;
(b) a combination of the nucleotide sequences as shown in SEQ ID NOS: 5, 2, 3, and 4;
(c) a combination of the nucleotide sequences as shown in SEQ ID NOS: 6, 7, 8, and 4;
(d) a combination of the nucleotide sequences as shown in SEQ ID NOS: 9, 10, 11, and 12; and
(e) a combination of the nucleotide sequences as shown in SEQ ID NOS: 23, 24, 15, 4, and 25; and then detecting the obtained amplified product.

2. A method of detecting *Streptococcus pneumoniae* comprising:

amplifying by isothermal amplification at least a portion of a lytA gene derived from *Streptococcus pneumoniae* using a loop-mediated isothermal amplification (LAMP) primer set, wherein the primer set is the combination of the nucleotide sequences as shown in SEQ ID NOS: 23, 24, 15, 4, and 25; and then detecting the obtained amplified product.

* * * * *